United States Patent [19]

Hochman

[11] Patent Number: 4,515,167
[45] Date of Patent: May 7, 1985

[54] DEVICE FOR THE DEVELOPMENT, TRAINING AND REHABILITATION OF THE PUBOCOCCYGEAL AND RELATED PERINEAL MUSCULATURE OF THE FEMALE

[76] Inventor: Joel S. Hochman, 121 Sandoval St., Santa Fe, N. Mex. 87501

[21] Appl. No.: 470,196

[22] Filed: Feb. 28, 1983

[51] Int. Cl.³ .................. A61B 10/00; A61N 1/36
[52] U.S. Cl. ................... 128/736; 128/738; 128/778; 128/788
[58] Field of Search ........... 128/639, 642, 736, 738, 128/784, 788, 419 R, 421, 422, 903, 778

[56] References Cited

U.S. PATENT DOCUMENTS

| | | | |
|---|---|---|---|
| 3,195,535 | 7/1965 | Westermann | 128/903 X |
| 3,236,240 | 2/1966 | Bradley | 128/903 X |
| 3,933,147 | 1/1976 | DuVall | 128/788 |
| 4,124,028 | 11/1978 | Gallo | 128/422 X |
| 4,387,719 | 6/1983 | Plevnik et al. | 128/421 |
| 4,387,724 | 6/1983 | Zartman | 128/738 X |
| 4,399,821 | 8/1983 | Bowers | 128/421 X |
| 4,406,288 | 9/1983 | Horwinski et al. | 128/788 X |

FOREIGN PATENT DOCUMENTS 1145749  3/1969  United Kingdom ............... 128/788

*Primary Examiner*—Lee S. Cohen
*Attorney, Agent, or Firm*—B. P. Fishburne, Jr.

[57] ABSTRACT

A completely portable and intravaginally contained myostimulatory device using biofeedback techniques in the treatment of vaginally related disfunctional syndromes is disclosed. The self-contained device is programmable and self-regulated as to frequency, duration and intensity of treatment. It can be worn for long periods of time in complete privacy and enables training in the control, mastery and improvement of strength of the vaginal musculature including the physiological functions associated with the Grafenburg Spot. The device may be equipped with cervical secretion viscosity and temperature-sensing transducers for the prediction of ovulation and the fertility period with a high degree of accuracy.

4 Claims, 6 Drawing Figures

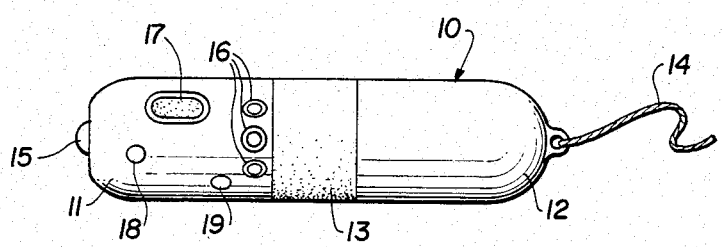
FIG.1
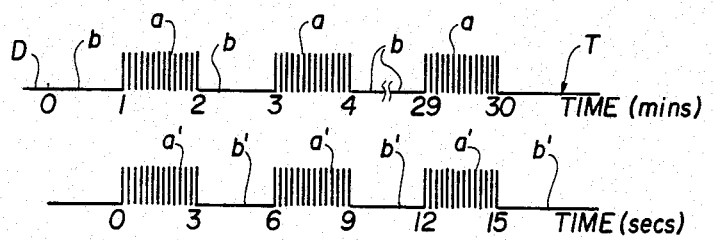
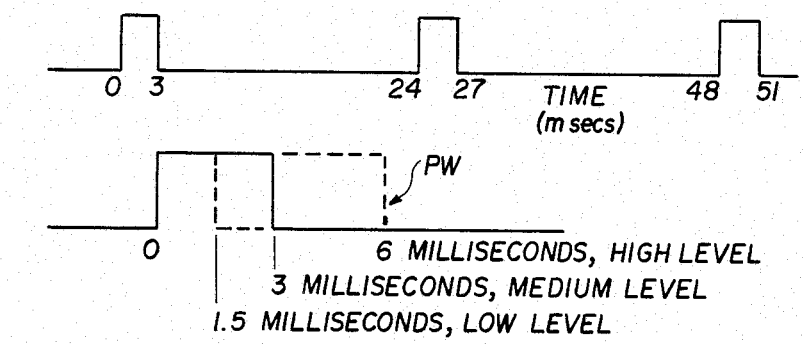
FIG.2
FIG.3
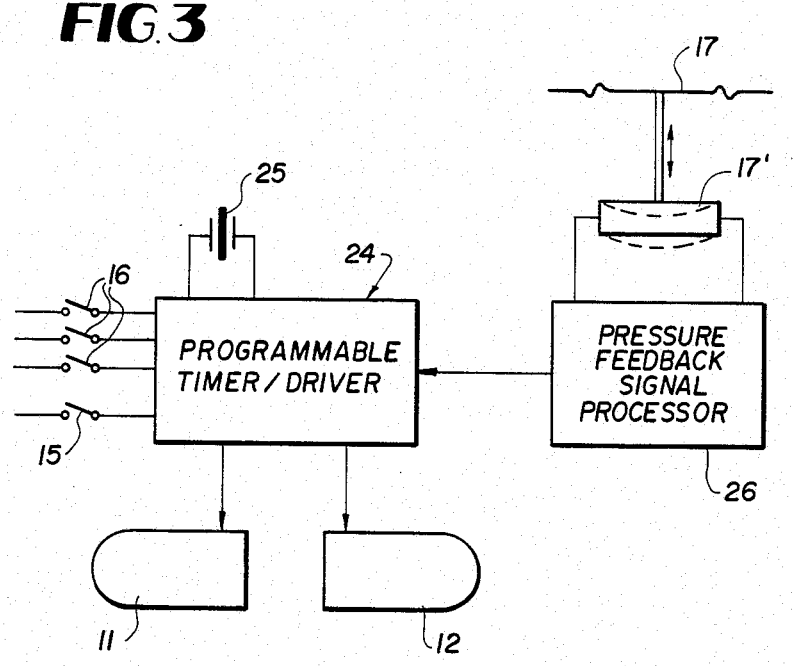

DEVICE FOR THE DEVELOPMENT, TRAINING AND REHABILITATION OF THE PUBOCOCCYGEAL AND RELATED PERINEAL MUSCULATURE OF THE FEMALE

BACKGROUND OF THE INVENTION

The present invention relates to electrical stimulation of the pubococcygeal and related musculature of the female perineum, including the "Grafenburg Spot". It is well known that lack of development, or deterioration, of the pubococcygeal musculature can result in numerous dysfunctions in the female. Urinary incontinence; sexual dysfunctions, including anorgasmia; syndromes of impaired arousal are all known to be associated with maldevelopment or deterioration of the integrity of the pubococcygeal musculature. Recent evidence also indicates that there is a strong correlation between development of the pubococcygeum and the ability to attain vaginal orgasm and ejaculation, related to stimulation of the "G-Spot" on the superior, anterior portion of the vagina.

Heretofore, treatment of these various conditions has been limited. Rehabilitative exercises (the Kegel exercises) have been available, though the effectiveness of the treatment is undemonstrated. Alternatively, a myostimulatory device has been available which has several critical limitations due to design and concept. A battery containing "handle" protrudes outside the vagina and must be held by the subject. Therefore, treatment is limited to the amount of time the subject can devote to holding the device in place. Further, no control of either frequency or duration of the stimulation is possible, and there is no means of monitoring the activity of the device or for incorporating biofeedback principles into the treatment.

By the present invention, there is provided a myostimulatory device which eliminates the need for the patient to hold the treatment device in place, and which eliminates any restrictions on the total duration of the treatment, or on the intensity, frequency or duration of the myostimulatory signals, and which utilizes biofeedback phenomena in its operation. Because the device is entirely intra-vaginally contained, the treatment may be given in total privacy and in any circumstances or locations. Also, the total duration of treatment, frequency and intensity of stimulation may be controlled as prescribed by a physician, or as individually desired by the patient.

The device provides complete portability and privacy of treatment. It eliminates the need to visit the physician or physician's assistant on any frequent or regular basis, and makes the extent of treatment a purely subjective decision, within the privacy of the patient's personal preferences.

SUMMARY OF THE INVENTION

One of the objects of the present invention is to provide a myoelectric stimulatory device of a size and shape that can be worn entirely inside the adult vagina, thereby allowing the user complete freedom of movement and activity while the device is in use.

Another object of the invention resides in a myostimulatory device which is programmable before insertion to set operating parameters, such as stimulation level, timing of the stimulation pulses, and total duration of a stimulation session.

A further object is to provide means for measuring the activity of the musculature being stimulated or voluntarily exercised to show the efficacy of the stimulation, to show the degree of voluntary control, to show the state of muscle tone, and to provide feedback information for a closed loop self-adjusting myoelectric stimulation system or to acquire voluntary control over the muscles by biofeedback techniques.

Availability of an internally worn device, by removing the constraints on movement and activity necessitated when an external device is used, allows the timing of the stimulation pulses to be set without the restraints of inconvenience. By allowing the stimulation pulses to be spaced further apart in time, the need is avoided for increasing the stimulation level during a session to compensate for fatigue or adaptation of the neuro-muscle system.

Versatile programmability of the stimulation pulse timing allows the stimulation program to be optimized for the best combination of efficacy, comfort, and convenience. A continuous sequence of alternate pulsing and not pulsing, as used with presently available equipment, may not even be close to optimum. The availability of programming will allow better optimization of the stimulus program for different types of patients, for patients in various stages of treatment, and for other variations among patients.

A means for measuring muscle activity allows the physician to know how the treatment is progressing independently of subjective judgments by the patient. One of the objectives of a treatment program may be acquisition of voluntary control over the muscles. When the patient does not have a sense of the state of tension or relaxation in these muscles, biofeedback supplies a method for developing such control. One of the requirements for biofeedback is a means by which the patient can tell what the bodily function in question is doing. A means for measuring the muscle activity with an audible or visual indication would supply this need. If one incorporates the sensing means in the same device as the stimulator, then it is in principle possible to make a closed-loop system in which the stimulation level is automatically adjusted for a desired level of stimulated muscle activity.

Measurements made on one of the presently available stimulatory devices with an external battery and pulsing circuit have established that adequate stimulation can be obtained with pulses of 3.0 volts or less and a duty cycle of about 12% during the ON part of a three-second ON and three-second OFF cycle. Average current flow between the stimulation electrodes is well below one milliampere. It is possible, using modern low voltage, low speed digital circuitry such as low voltage CMOS or integrated injection logic to generate such a signal with very little overhead power loss, using a constant voltage power supply and pulse-width modulation of the stimulation pulses to control stimulation level.

A circuit with programmable timing and programmable stimulus levels can be built using a supply voltage of about 2.5 to 3.0 volts and consuming about one milliampere. A suitable battery of this voltage and a capacity of about 160 milliampere hours can be obtained in a cylindrical package of about half an inch in diameter and about half an inch long with a pair of silver-oxide cells, a single lithium cell, a pair of mercury cells, etc. Because the device package is preferably about three quarters of an inch in diameter and about three inches long, such a battery will fit in less than half the available internal volume, allowing the rest to be used for the stimulus control and drive circuitry and for the measurement circuitry, if used.

The required stimulus timing and drive circuitry is of lesser complexity than that used in many electronic digital watches and can easily be incorporated onto a single integrated silicon circuit, such as those used in digital watches. As is done in digital watches, programming instructions can be entered by means of one or more miniature pushbutton switches. The potentially low cost of such an integrated circuit, along with the expected one or two hundred-hour operating time from a battery makes it possible to consider building a stimulating device as a sealed unit with a factory-installed, non-replaceable battery. Such a sealed unit, as compared with one allowing battery replacement, would have the advantages of lower package complexity and cost, smaller size, much less likelihood of leakage of fluids into or out of the package, no need for limiting the selection of batteries to those available through retail channels for replacement purposes, and no possibility for tampering with the contents.

The muscle function measurement could be implemented with a force measurement sensor such as a strain-sensitive thin film or semiconductor sensor suitably coupled to a flexible member on the case of the device. Alternatively, a pressure-sensitive resistive polymer composite can be used, as are now commonly used in some touch-sensitive switches. The measurement information can be transmitted from the package by radiotelemetry. One possible means useful in cases where long battery life is not necessary is audio modulation of a low-power fm transmitter using a locally unused frequency in the commercial fm band. This has the advantage that suitable fm receivers are widely available. A telemetry means with much lower power requirements is modulated backscatter of an externally supplied incident cw rf signal. This does, however, require the use of a specially designed "interrogator" device to receive the signal and supply the rf illumination field. In either case, the information transmission system can share the electrodes used to carry the stimulation signal, acting as a dipole antenna. In either case also, the usable range is very small, but long enough for the purpose. A particular advantage of the modulated-backscatter radiotelemetry method is that power drain can be made much less than one milliampere and the information sending circuitry is very simple and small, making it practicable to incorporate such a telemetry transmitter in the same device that holds the stimulating circuitry.

It has been shown that the objectives set out for the present invention can be met by using presently available technology, some of which has become available for commercial use only within the past several years. The key technology for the stimulus circuitry is low-voltage, low-power digital integrated circuitry, which makes implementation of that function possible with a battery small enough to fit inside the package. The key technology for the measurement and telemetry function is that of miniature strain gauges, integrated telemetry circuitry, and the development of practicable modulated-backscatter telemetry.

Building upon the basic technology of the device as thus far discussed, it is easy to perceive the opportunities which the device affords in other applications to bio-engineering. Specifically, the device may be equipped with cervical secretion viscosity (CSV) and temperature-sensing transducers to provide both the subject and her clinician with essential information as to these parameters. For example, the combination of CSV and temperature together predict a woman's ovulation and fertility period with greater than 90% accuracy. Thus, by a simple expansion of the technology on which the basic device is based, data can be provided as to vaginal temperature and CSV, and by means of state-of-the-art micro-chip technology this data can be averaged and compared to a preprogrammed norm, in order to trigger an appropriate signal built into the device, or, to remotely signal the wearer and/or her clinician of ovulation and probable fertility, within defined limits. Thus, by a simple modification of the basic device, an extremely reliable means of identifying ovulation and the period of likely fertilization is realized. This, in turn, provides an aid to both conception and contraception, based entirely upon natural biological principles.

Accordingly, an added objective of the invention is to utilize its bio-electronic capabilities to monitor the human or other mammalian cervical mucus and CSV, as well as vaginal temperature, for purposes of identifying the period of likely fertility and conception. Conversely, such information can also be used predictively to prevent conception.

Availability of the internally worn device enables periodic sampling of CSV and temperature data, averaging of the data, and a comparison of the data to the anticipated normal menstrual cycle of the user. Established medical knowledge indicates that both CSV and basal body temperature undergo a distinctive change at the time of ovulation in the menstrual cycle. Thus, the data obtained by the device may be compared to the expected cycle, to predict the fertile period of the user. Some experts have reported that with the use of these bio-metric data, greater than 90% accuracy can be obtained in identifying ovulation and the fertile period.

The required monitoring and telemetry circuitry is of lesser complexity than that used in many contemporary electronic watches, and can be easily incorporated onto a single silicon circuit, such as those used in digital watches. As is done in digital watches, programming instructions can be entered by means of one or more miniature push button switches. The potentially low cost of such an integrated circuit, along with the expected one or two hundred hour operating time from a battery, makes it possible to consider building a stimulating biomonitoring device as a sealed unit having a factory installed, non-replaceable battery. Such a sealed unit, as compared to one allowing battery replacement, would have the advantages of lower package complexity and cost, smaller size, with less likelihood of leakage of fluids into or out of the package, no need for limiting the selection of batteries to those available through retail channels for replacement purposes, and no possibility for tampering with the contents.

The CSV and temperature measurement can be implemented with digital transducers, averaged and "remembered" by the circuitry, compared to a pre-programmed predicted cycle of data events, and the results transmitted from the package by radio-telemetry. One possible means useful in cases where long battery life is not necessary is audio modulation of a low power FM transmitter using a locally unused frequency in the commercial FM band. This has the advantage that suitable FM receivers are widely available. A telemetry means with much lower power requirements is modulated backscatter of an externally supplied incident cw rf signal. This does, however, require the use of a specifically designed "interrogator" device to receive the signal and supply of the rf illumination field. In either case, the information transmission system can share the electrodes used to carry the stimulation signal, acting as a dipole antenna. In either case, also, the usable range is very small, but long enough for the purpose. A particular advantage of the modulated-backscatter radiotelemetry method is that power drain can be made much less than one milliampere and the information sending circuitry is very simple and small, making it practical to incorporate such a telemetry transmitter in the same device that holds the stimulating and measuring circuitry.

It has been shown that the objective set out for the present invention can be met by using presently available technology, some of which has become available for commercial use only within the past several years. The key technology for the stimulating and monitoring circuitry is low-voltage, low-power digital intergrated circuitry, which makes implementation of the functions possible with a battery small enough to fit inside the package. The key technology for the measurement and telemetry function is that of miniature CSV and temperature transducer, intergrated telemetry circuitry, and the development of practical modulated-backscatter telemetry.

Other features and advantages of the invention will become apparent to those skilled in the art during the course of the following description.

BRIEF DESCRIPTION OF THE DRAWINGS

FIG. 1 is an assembled side elevation of an intravaginal muscle stimulator and fertility monitoring device.

FIG. 2 is a stimulus pulse timing diagram.

FIG. 3 is a block diagram of a programmable intravaginal myoelectric stimulator with pressure feedback.

DETAILED DESCRIPTION

Figure 6:
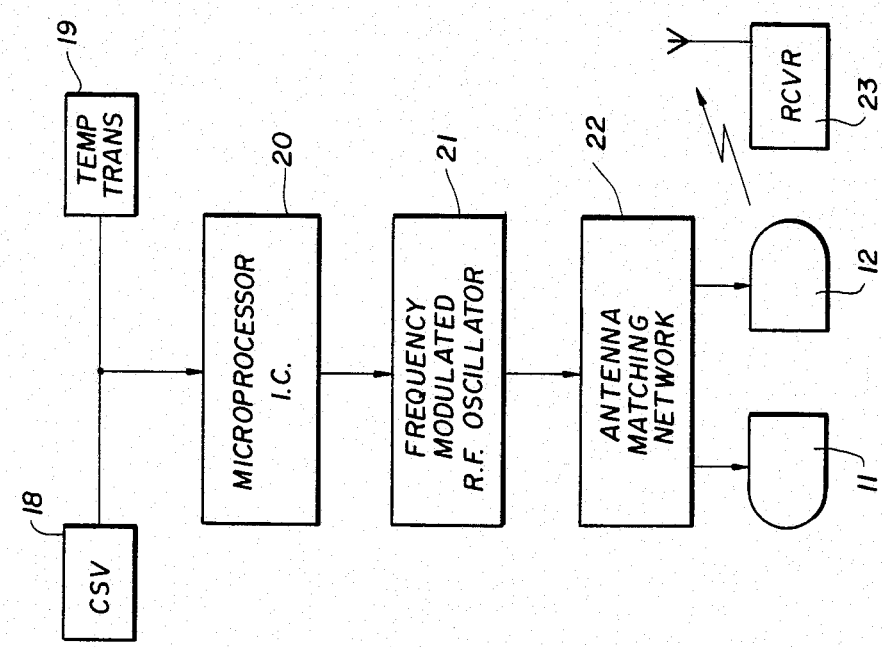
FIG. 6 is a block diagram of a CSV and temperature measuring, averaging/analyzing and telemetry system.

Referring to the drawings in detail wherein like numerals designate like parts, and referring first to FIG. 1, an assembled intravaginal myoelectric stimulator device 10 in its most general and comprehensive form includes the stimulus, muscle response, measurement functions, CSV, and temperature. In some cases, the stimulator device can be made without the CSV and temperature monitoring capability.

The exterior of the device 10 consists of two case/electrode sections 11 and 12 and a central insulating member 13. A flexible retrieval cord 14 is attached to one end of the device to facilitate its removal after use. The overall dimensions of the device are preferably about ¾" in diameter by about 3" long, with rounded ends and a smooth exterior surface for ease of insertion and retrieval.

The metal case sections 11 and 12 serve both as parts of the protective case and as the electrodes for the stimulating function. The metal is a biologically compatible type where it is in contact with the vaginal wall tissue. A way to insure this while improving surface conductivity over some other metals, such as stainless steel, is to apply a thin gold plate. A very thin additional coating of a catalytically active metal, such as platinum or palladium, may be useful to speed up recombination of the products of electrolysis at the electrode surfaces, such as oxygen, hydrogen and chlorine.

The central insulating member 13 separates the two electrodes 11 and 12 and forms a part of the protective case or shell. It may be formed of a ceramic having a smooth glaze, or from one of a number of known biologically compatible plastics. If a replaceable battery is used, the metal case/electrode 12 is fitted into the insulating member 13 with screw-threads and a suitable elastomeric seal to minimize leakage of fluids into or out of the joint. If a non-replaceable battery is used, both metal case/electrode sections 11 and 12 can be permanently sealed to the central insulating member 13 by means of a chemical bonding agent, when the member 13 is formed of plastics. If this member is a ceramic member, the engaging surfaces of the ceramic member may be metallized, and the elements 11, 12 and 13 may be permanently assembled by brazing.

An end push button switch 15 is employed to turn on the device to start the stimulus session and is operable by finger pressure. The switch 15 operates through a small bellows-type section formed in the metal case section 11 and does not form an opening in the case. Accidental additional operation of the switch 15, as for example during insertion of the device into the vagina, does not matter as it will not alter the function of the device once an operating cycle has been started by the first activation of the switch 15.

Programming switches 16 on the case section 11 are miniature switches operated by a pointed object such as a ball point pen. These switches are similar to those found on some digital watches and are state-of-the-art components. All of the switches are operated through miniature bellows formed in the metal case, and therefore do not compromise sealing. The switches 16 are used to program the stimulus timing and level, and would normally be seldom used after initial set-up. Since these switches require deliberate action to operate, it is highly unlikely that they would ever be inadvertently operated.

A pressure sensor flexible diaphragm 17 is set into the exterior of metal case section 11 and is coupled to an internal strain measuring sensor element 17', as shown in FIG. 3. While the drawing, FIG. 1, shows the diaphragm 17 set into the metal case/electrode section 11, this diaphragm could, in some cases, be on the case/electrode section 12, depending on manufacturing convenience and internal space availability. If desired, a plurality of pressure sensing elements can be distributed around the surface of the device to obtain an even more representative measure of the muscle response to stimulation.

In the comprehensive embodiment of the invention, FIGS. 1 and 6, CSV and temperature transducers 18 and 19 are set into the exterior of case section 11 in spaced relationship and are coupled with the integrated measurement and telemetry circuitry shown in FIG. 6, this circuitry including a microprocessor 20, a frequency modulated rf oscillator 21, and an antenna matching network 22. An FM radio receiver 23 at a convenient location receives an FM signal generated by the arrangement in FIG. 6 to alert the wearer of the device of ovulation and the probable fertility period, as discussed previously.

FIG. 2 of the drawings depicts an example of a stimulus pulse train which can be programmed into the device. It should be understood that the invention is not limited to this particular arrangement shown in FIG. 2. The total time T, shown in FIG. 2 as one-half hour, starts with the operation of switch 15 and ends on a pre-programmed signal from the internal timer 24, FIG. 3, of the device. Within this "stimulus session", the time is further sub-divided into alternating cycles a of stimulation and rest b, shown in FIG. 2 as being about one minute each. Within these stimulation cycles, there are further subdivisions a' and b' into periods when stimulus pulses are applied periodically, and periods when the muscle is allowed to relax. In the example shown in FIG. 2, these are indicated as being about three seconds each. The stimulus pulses are of constant voltage and with a constant period, indicated in FIG. 2 as being 3 volts and 24 milliseconds, respectively. The widths of the stimulating pulses may be varied by programming to control the stimulation level. In the illustrated example, the stimulus pulse width is shown as 3 milliseconds as a "medium" stimulus level. To reduce the stimulus level, the pulse width is reduced, for example, to 1.5 milliseconds. To increase the stimulus level, pulses are made longer, for example, to 6 milliseconds. These pulse width variations are graphically illustrated at PW in FIG. 2. Intermediate choices of pulse width could also be made available.

For the sake of economy in manufacturing the electronic control circuitry, it is most convenient to make all of the times multiples of a primary clock period in a binary sequence of values, but in general any arbitrary multiples can be used. For example, in electronic watch circuitry, multiples using a base of three are common. Many other variations in the pulse timing program are possible and can be incorporated in the design of the programmable timer 24 which is state-of-the-art equipment and which includes a resonator element 25, FIG. 3. For example, an initial delay period, as indicated in FIG. 2 at D, can be used to allow time to insert the device before the stimulus pulses start. Also, the stimulus pulse width can be varied inside the three second pulsing cycle to gradually increase the stimulus level during the cycle.

That such versatile programming is possible in a device of this size at low cost in power consumption is demonstrated by the availability of low cost digital watches, which perform timing functions of greater complexity than those described herein.

FIG. 3 shows in block diagram form a stimulating device incorporating closed loop feedback to set the stimulus level so as to produce a desired degree of muscle activity. A simpler form of the device would omit this feedback function and employ a pre-set stimulus level. No details of the programmable timer 24 are shown, and such details are not necessary, as the methods for producing this function are well known in the art and per se are not a part of the invention. In the preferred embodiment of the invention, the programmable timer 24 would be fabricated in a low voltage, low current process, such as silicon-gate complementary metal oxide semiconductor (silicon state CMOS), which has the property of drawing only "leakage" current in those portions of the circuitry which are not being cycled. With such an integrated circuit, the battery power can remain impressed on the circuit between use periods, without discharging the battery, and avoiding the necessity for a mechanical on-off switch. The circuit can be triggered into operation by means of a trigger signal supplied by the start switch 15 and triggered off when the pre-programmed timer has timed out. The basic time standard can be provided with a quartz crystal resonator, previously indicated at 25, as is done in electronic watches. Alternatively, a resistor-capacitor timing circuit could be utilized in some cases.

Circuitry to be used with the pressure sensor 17' is also an adaptation of functions standard in the industry and need not be dealt with in detail herein. The signal processing circuitry 26, FIG. 3, can accept information from the pressure sensor 17', probably in the form of a pressure-sensitive resistance, and transform the information into digital form for interfacing with the digital stimulus level control circuitry. The pressure sensing circuitry can be incorporated onto the same integrated circuit chip used for the programmable timer 24 or can be on a separate chip. Power for the pressure sensing circuitry is turned on and off by the timer chip to conserve power during the times when the device is not in use.

Figure 4:
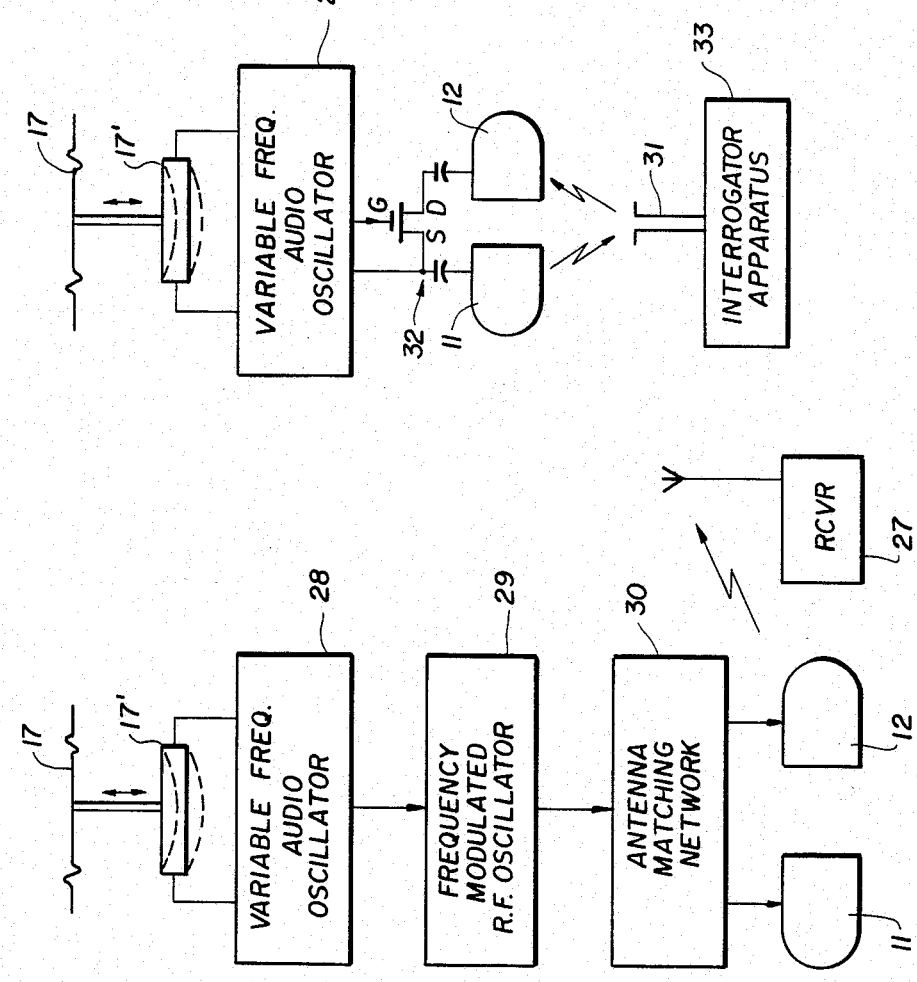
FIG. 4 is a block diagram of intravaginal muscle function sensor and telemetry system.

FIG. 4 shows in block diagram form an intravaginal device for telemetering muscle function information to an FM radio receiver 27. In the embodiment shown, a manually operated switch turns the power to the circuitry on and off but alternatively a programmed timer could be included to turn the power off after a preset time. Information from the pressure sensor 17' or averaged information from a plurality of such sensors is used to vary the frequency of an audible frequency tone generator 28, and this frequency in turn is used to frequency modulate a low power rf generator indicated at 29 in FIG. 4, which in this example is set to a frequency in the commercial FM broadcast band. The rf generator output is coupled to the device's metal case sections 11 and 12 acting as a dipole antenna, using a suitable coupling network 30 to match between the generator 29 and the electrically-short antenna formed by the case sections 11 and 12. Alternatively, the retrieval cord 14 could be made of conductive material and thus be made part of the antenna.

It is known that rf signals in the frequency range of the commercial FM broadcast band propagate relatively efficiently through body tissue, and the dipole antenna formed by a 3" long device can be driven reasonably efficiently at such frequency. The use of the commercial FM broadcast band is also convenient, in that the receivers for such signals are widely available at low cost. Low power signals at transmitted powers of 5 milliwatts or less can be used in the United States and other parts of the world without interference to other users of the frequency, and without licensing by the Government Agency in charge of rf frequency usage. Systems based on the use of the commercial FM broadcast band are probably the most commonly used types of biotelemetry apparatus.

For biofeedback purposes, aural feedback by listening for pitch changes in the received signal would probably be sufficient. For quantitative measurements, one could attach a frequency counter to the FM receiver, for example by means of the earphone or audio out jack available on many receivers.

Figure 5:
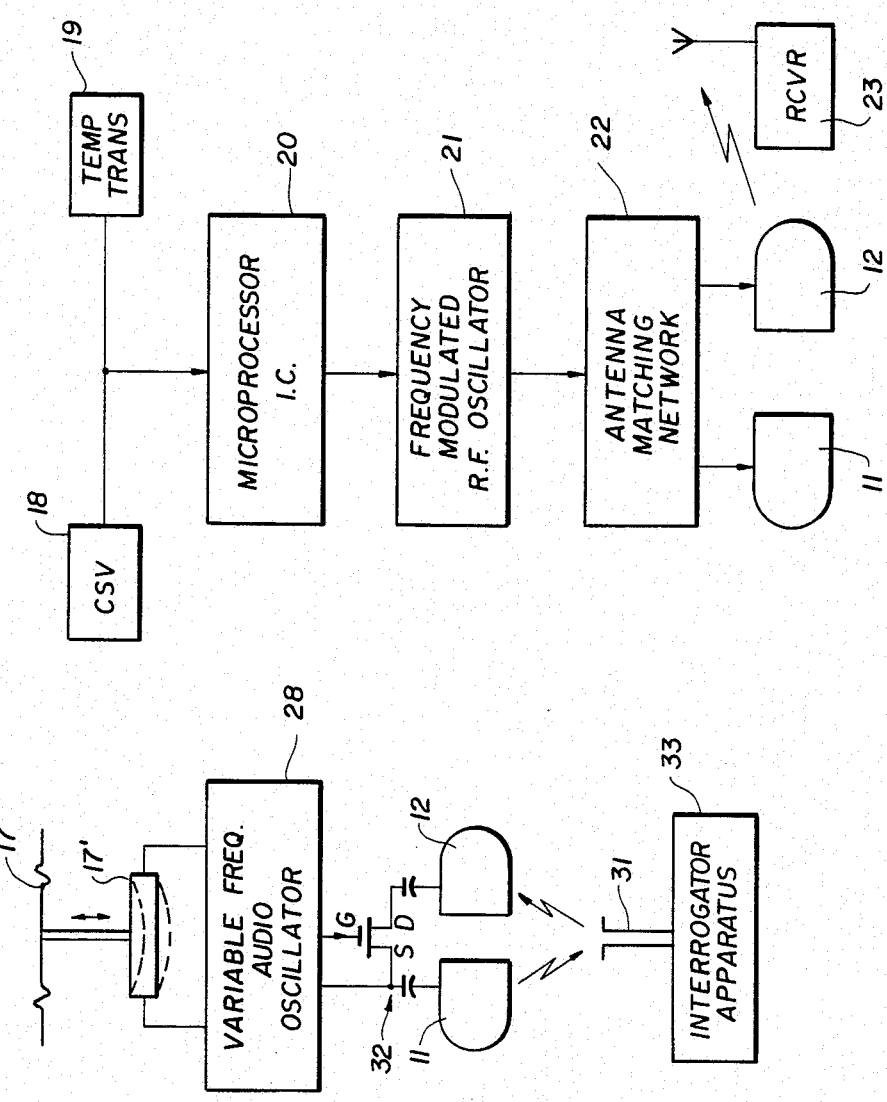
FIG. 5 is a block diagram of an intravaginal muscle function sensor and telemetry system using modulated backscatter of an incident rf illumination signal.

FIG. 5 shows in block diagram form a muscle function telemetry system based on the use of modulated rf backscatter. The use of modulated backscatter for telemetry transmission, a fairly recent development, offers the advantages of very simple, low cost, and compact circuitry at the transmitting end and extremely low power consumption. The modulated backscatter sending device does not generate an rf carrier of its own, but rather varies the amplitude of the amount of carrier signal supplied from the outside which is "scattered" or reflected from a resonant antenna. The reflected or scattered signal is received at an interrogator antenna 31 where it is mixed with a sample of the illuminating rf signal and detected by the "homodyne" method. Special techniques are now available to avoid loss of the signal when the incoming and reference signals are in phase quadrature, making possible a practical telemetry system based on modulated backscatter. A backscatter modulator 32, FIG. 5, is coupled between the oscillator 28 and the two metal cases sections 11 and 12, as shown.

A present disadvantage of modulated backscatter telemetry is that a specially designed interrogator/receiver apparatus 33 must be used to receive the signal. However, the important advantages of compact and low power transmitting circuitry appear to be sufficient to warrant the investment in some applications of the invention.

From the foregoing, the construction, manufacture and operation of this myostimulatory treatment device for the pubococcgeal and related perineal musculature of the female, with or without a monitoring feature to detect ovulation and fertility, will be readily understood and further explanation is believe to be unnecessary. However, as numerous modifications and changes will readily occur to those skilled in the art, it is desired not to limit the invention to the exact constructions shown and described, and accordingly all suitable modifications and equivalents are included which fall within the scope of the claimed invention.

I claim:

1. A device for monitoring CSV and temperature to thereby predict ovulation and fertility periods comprising a casing having a size and shape whereby it can be contained bodily and entirely within the vagina, the casing including metallic parts on the exterior surface thereof adapted to serve as a dipole antenna, an integrated circuit inside of the casing including a signal averager and comparator, said integrated circuit also including an antenna matching network connected with said metallic parts, and CSV and temperature sensing transducers on the casing and adapted to contact the vaginal wall and being electrically connected with said integrated circuit.

2. A stimulating and monitoring device adapted to be entirely contained in the vagina comprising a casing including metallic parts on the exterior surface of the casing serving as electrodes and being adapted to contact the vaginal wall, the metallic parts also serving as a dipole antenna, circuitry including a power source and means to generate electrical stimulation to the vaginal wall through the metallic parts contained in said casing, said circuitry including a programmable timer, a pressure-sensing signal emitting element, a pressure feedback signal processor connecting the programmable timer and the pressure-sensing signal emitting element and an antenna matching network connected to said metallic parts, a manual switch operably mounted on the exterior of the casing and connected to the programmable timer to energize said circuitry, programming switches operably mounted on the exterior of the casing for regulating the intensity, amplitude and time period of stimulation produced by the device and being connected to said programmable timer, a pressure sensing yielding element on the casing adapted to engage the vaginal wall and being connected with said pressure-sensing signal emitting element, and CSV and temperature transducer elements on the casing and being connected with the circuitry, and the circuitry further including a signal averager and comparator for the signals delivered by said transducer elements and being connected to said matching network.

3. A device as defined in claim 2, and the signal averager and comparator comprising a computer, an rf oscillator and said antenna matching network coupled with said metallic parts.

4. A device for the development, training and rehabilitation of the pubococcygeal and related perineal musculature of the female comprising a casing of a size and shape to permit wearing the device bodily and entirely within the vagina, said casing including metallic parts forming electrodes on the exterior surface of the casing and adapted to be in contact with the wall of the vagina whereby the device may deliver electrical stimulation to such wall when energized, electrical circuitry including a power source and means to generate electrical stimulation contained wholly within the casing and including connections with the metallic parts forming said electrodes, programmable switching means on the device whereby said circuitry can be energized for a predetermined period of time followed by automatic de-energizing of the circuitry and termination of the stimulatory cycle of the device, said metallic parts also serving as antenna components, the circuitry further including an audio oscillator and a backscatter modulator coupled with said metallic parts, and a pressure-sensitive transducer coupled between the exterior of the casing and the audio oscillator.

* * * * *